United States Patent
Zhang et al.

(10) Patent No.: US 12,338,482 B2
(45) Date of Patent: Jun. 24, 2025

(54) ULTRALOW CONCENTRATION SENSING OF BIO-MATTER WITH PEROVSKITE NICKELATE DEVICES AND ARRAYS

(71) Applicant: Purdue Research Foundation, West Lafayette, IN (US)

(72) Inventors: Haitian Zhang, Lafayette, IN (US); Fan Zuo, Terre Haute, IN (US); Feiran Li, West Lafayette, IN (US); Jong Hyun Choi, West Lafayette, IN (US); Shriram Ramanathan, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 929 days.

(21) Appl. No.: 17/311,707

(22) PCT Filed: Dec. 10, 2019

(86) PCT No.: PCT/US2019/065333
§ 371 (c)(1),
(2) Date: Jun. 8, 2021

(87) PCT Pub. No.: WO2020/131475
PCT Pub. Date: Jun. 25, 2020

(65) Prior Publication Data
US 2022/0025425 A1    Jan. 27, 2022

Related U.S. Application Data

(60) Provisional application No. 62/782,068, filed on Dec. 19, 2018.

(51) Int. Cl.
*C12Q 1/00*    (2006.01)
*A61B 5/145*    (2006.01)
(Continued)

(52) U.S. Cl.
CPC .......... *C12Q 1/005* (2013.01); *A61B 5/14532* (2013.01); *A61B 5/1486* (2013.01); *C12Q 1/006* (2013.01); *G01N 33/48707* (2013.01)

(58) Field of Classification Search
CPC .... C12Q 1/005; C12Q 1/006; A61B 5/14532; A61B 5/1486; A61B 5/14546; G01N 33/48707; G01N 33/553
See application file for complete search history.

(56) References Cited

U.S. PATENT DOCUMENTS

| | | | | |
|---|---|---|---|---|
| 2004/0040868 A1* | 3/2004 | DeNuzzio | ............. | B01L 3/5085 205/792 |
| 2015/0366493 A1* | 12/2015 | Cremers | ............. | A61B 5/4362 205/264 |
| 2016/0248006 A1* | 8/2016 | Shi | ......................... | H10N 70/24 |

FOREIGN PATENT DOCUMENTS

| | | | | |
|---|---|---|---|---|
| WO | WO-2016140543 A1 * | 9/2016 | ............... | C12Q 1/00 |
| WO | 2018106625 | 6/2018 | | |

OTHER PUBLICATIONS

Wang et al. (2010). "A novel sensitive nonenzymatic glucose sensor based on perovskite LaNi0.5Ti0.5O3-modified carbon paste electrode". Sensors and Actuators B: Chemical, 151(1), 65-70. (Year: 2010).*

(Continued)

*Primary Examiner* — Aaron J Kosar
*Assistant Examiner* — Andrew T Moehlman
(74) *Attorney, Agent, or Firm* — Pudue Research Foundation

(57) ABSTRACT

Disclosed herein is an ultralow concentration sensor of biomarkers, and the use thereof to help heath industry, medical centers and food industry to sense biomarkers by catalyst assisted charge transfer from the biomarkers to the sensor device, resulting increased electrical resistance of the sensor. Specifically, perovskite nickelate $RNiO_3$ is used to (Continued)

sense biological material facilitated by specific enzymatic activity in the proximity.

7 Claims, 3 Drawing Sheets

(51) Int. Cl.
 *A61B 5/1486* (2006.01)
 *G01N 33/487* (2006.01)

(56) References Cited

OTHER PUBLICATIONS

Translation of Cho et al. WO-2016140543-A1. Obtained from Espacenet on Jul. 26, 2024. Available at <https://worldwide.espacenet.com/publicationDetails/biblio?CC=WO&NR=2016140543A1&KC=A1&FT=D> Original document available Sep. 9, 2016 (11 pages total). (Year: 2016).*

Lee et al. 2018. "Enzyme-based glucose sensor: from invasive to wearable device". Advanced healthcare materials, 7(8), p . 1701150 (14 p. total). (Year: 2018).*

Raghu et al. 2014. "A novel horseradish peroxidase biosensor towards the detection of dopamine: A voltammetric study." Enzyme and microbial technology 57 (2014): 8-15.Enzyme and Microbial Technology 57: 8-15 (Year: 2014).*

Wang et al. 2017. "Perovskite-type calcium titanate nanoparticles as novel matrix for designing sensitive electrochemical biosensing". Biosensors and Bioelectronics, 96, pp. 220-226 (Year: 2017).*

Huang, Ke-Jing, et al., "Sub-Femtomolar DNA Detection Based on Layered Molybdenum Disulfide/Multi-Walled Carbon Nanotube Composites, Au Nanoparticle and Enzyme Multiple Signal Amplification", Biosensors and Bioelectronics, 55, (2014) pp. 195-202.

International Search Report for International Application No. PCT/US19/65333, dated Feb. 18, 2020, (3 pages).

* cited by examiner

ULTRALOW CONCENTRATION SENSING OF BIO-MATTER WITH PEROVSKITE NICKELATE DEVICES AND ARRAYS

CROSS-REFERENCE TO RELATED APPLICATION

This U.S. application is a national stage entry under 35 U.S.C. § 371 (b) of International Application No. PCT/US19/65333, filed on Dec. 10, 2019, which is related to and claims the priority benefit of U.S. Provisional Application No. 62/782,068, filed Dec. 19, 2018, the contents of which are hereby incorporated by reference in their entireties.

GOVERNMENTAL RIGHT

This invention was made with government support under Grant No. 1609898 awarded by the National Science Foundation (NSF), under grant No. FA9550-16-1-0159 awarded by the Air Force Office of Scientific Research (AFOSR), and under Grant No. N0014-15-1-2707 awarded by the Office of Naval Research (ONR). The government has certain rights in the invention.

FIELD OF INVENTION

This disclosure is related to novel devices and arrays to detect ultralow concentration of bio-matter in physiological conditions. Specifically, perovskite nickelate $RNiO_3$ is used to sense biological material facilitated by specific enzymatic activity in the proximity.

BACKGROUND

Nickel forms a series of mixed oxide compounds which are commonly called nickelates. A nickelate is an anion containing nickel or a salt containing a nickelate anion, or a double compound containing nickel bound to oxygen and other elements. Nickel can be in different or even mixed oxidation states, ranging from +2, +3 to +4. The anions can contain a single nickel ion, or multiple ions to form a cluster ion. The solid mixed oxide compounds are often insulating, but can also be metallic. They have a variety of electrical and magnetic properties. Rare-earth elements form a range of perovskite nickelates, in which the properties vary systematically as the rare-earth element changes. Fine-tuning of properties is achievable with mixtures of elements, applying stress or pressure, or varying the physical form.

Rare-earth nickelates with nickel in a +3 oxidation state have an electronic configuration similar for cuprates and so are of interest to high-temperature superconductor researchers. Other rare-earth fickelates can function as fuel cell catalysts. The ability to switch between an insulating and a conducting state in some of these materials is of interest in the development of new transistors that have higher on to off current ratios.

Despite the physical features of these rare earth materials are studied in conductor industry, the exploration of rare-earth nickelates in health care or medical devices is in its infancy or non-existent.

SUMMARY OF THE INVENTION

This disclosure provides biomolecule sensing devices based on enzyme-mediated spontaneous hydrogen transfer from bio-markers which function at body temperature in brain and in biological environments (e.g. artificial cerebrospinal fluid). The devices could be broadly used in health sciences, brain interfaces and biological routes to dope emerging semiconductors.

One embodiment of the instant disclosure provides an ultrasensitive device for detecting low concentration of biomarker in a biological fluid. The device comprises:

a perovskite nickelate film comprising RNiO3 or strongly correlated oxides such as transition metal oxide (eg. NiO, FeOx), wherein the perovskite nickelate film is configured as a lattice or with micro-fluidic channels, wherein R is selected from the group consisting of Sm, Nd, Eu, Gd, Dy, Y, Lu, Pr, and La; and an enzyme or other catalyst conjugated to a conductive material, wherein the conductive material is associated with said perovskite nickelate film or in close proximity to the perovskite nickelate film, wherein the enzyme or other catalyst facilitates hydrogen transfer from the biomarker to the perovskite nickelate film and reduces conductivity at the interface between the perovskite nickelate film and the biomarker.

In one preferred embodiment the aforementioned device further comprises an electrode, wherein the electrode captures increased resistivity in the perovskite nickelate film.

In one preferred embodiment the conductive material in aforementioned device is Au electrode.

In one preferred embodiment the enzyme in aforementioned device is glucose oxidase and the biomarker is glucose in body fluid, such as blood, sweat or urine.

In one preferred embodiment the enzyme in aforementioned device is horseradish peroxidase (HRP) and the biomarker is dopamine in cerebrospinal fluid.

In one preferred embodiment enzyme in aforementioned device is conjugated to Au electrode surface via cystamine.

In one preferred embodiment the enzyme in aforementioned device is configured as arrays with large-scale circuits on a single chip, wherein various enzymes or other catalysts are conjugated to the arrays rendering specificity to different biomarkers simultaneously in the single chip.

The disclosure provides a method of detecting ultra-low concentration of biomarker in biological fluid. The method comprises the following steps:

Providing a device comprising following components:
a perovskite nickelate film comprising RNiO3 or strongly correlated oxides with similar transition metal oxide (eg. NiO, FeOx), wherein the perovskite nickelate film is configured as a lattice or with micro-fluidic channels, wherein R is selected from the group consisting of Sm, Nd, Eu, Gd, Dy, Y, Lu, Pr, and La; and an enzyme or other catalyst conjugated to a conductive material, wherein the conductive material is associated with the perovskite nickelate film or in close proximity to the perovskite nickelate film, wherein the enzyme or other catalyst facilitates hydrogen transfer from the biomarker to the perovskite nickelate film and increases the resistivity of nickelate film;

Measuring the resistance reading $R_0$ between the device and the conductive material;

Immersing the device to a biological fluid;

Measuring the resistance reading R between the device and the conductive material after the immersing step; and Identifying the biological fluid with ratio of $R/R_0$ greater than 1 as the sample comprising said enzyme targeted biomarker.

In some preferred embodiment the aforementioned method is used to detect glucose in the biological fluid.

In some preferred embodiment the aforementioned method is used to detect dopamine in cerebrospinal fluid.

In some preferred embodiment the aforementioned method is conducted at room temperature or body temperature.

In some preferred embodiment the aforementioned method is to detect concentrations of biomarker between the ranges of about $10^{-16}$ M to about $10^{-17}$ M.

In some preferred embodiment the device in aforementioned method comprising Au as the conductive material.

In some preferred embodiment the device in aforementioned method comprising an enzyme selected from the group consisting of glucose oxidase and Horseradish peroxidase (HRP).

In some preferred embodiment the device in aforementioned method is configured as arrays with large scale circuits on a single chip to simultaneously sense various biomarkers that corresponding enzymes or other catalysts specifically recognize and facilitate hydrogen transfer.

In some preferred embodiment the aforementioned method further comprising integrating the device into a wearable electronic platform for personal healthcare monitoring.

In some preferred embodiment the aforementioned method is conducted in room temperature or body temperature.

In some preferred embodiment the aforementioned method is conducted spontaneously with biological fluid immersion of the device and free of external energy input.

This disclosure further provides a method for detecting ultra-low concentration of biomarker in a sample. The method comprises the following steps:

Providing a perovskite nickelate film having strongly correlated oxides from rare-earth or related transition metal oxides;

Providing a catalyst that may act on the biomarker in the sample and alter the physical property of the film, wherein the catalyst is in close proximity to the film;

Contacting the film with the sample; and

Measuring the film's optical, magnetic or thermal properties before and after said contact to determine the existence of the biomarker.

These and other features, aspects and advantages of the present invention will become better understood with reference to the following figures, associated descriptions and claims.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Functional interfaces between electronics and biological matter are essential to diverse fields including health sciences (e.g. detection of early stage diseases), soft robotics (e.g. sensory interfaces for autonomous systems), bio-engineering and search for life in extreme environments in land or water bodies on Earth, other planets or asteroids. Energy and information flow in biological and living matter occurs through ionic currents, however in traditional semiconductor devices, it is due to electrons and holes. Functional interfaces between biological and synthetic matter therefore can greatly benefit from simultaneous ion-electron transfer coupled with signaling capability in a range of biological and body/brain environments. Synthetic matter that responds to reaction intermediates at low concentrations therefore can be game-changing in this context, however must be functional near room (or body) temperature while constantly exposed to complex biological media. As a promising candidate, the perovskite nickelate $SmNiO_3$ (SNO, space group Pbnm), is water-stable, and belongs to a class of strongly correlated quantum materials, whose properties are highly sensitive to the occupancy of electrons in their partially-filled orbitals. When doped with charge carriers, SNO shows massive electronic structure changes: For one electron/unit cell doping from hydrogen, the electrical resistance changes by ~10 orders of magnitude.

Figure 2:
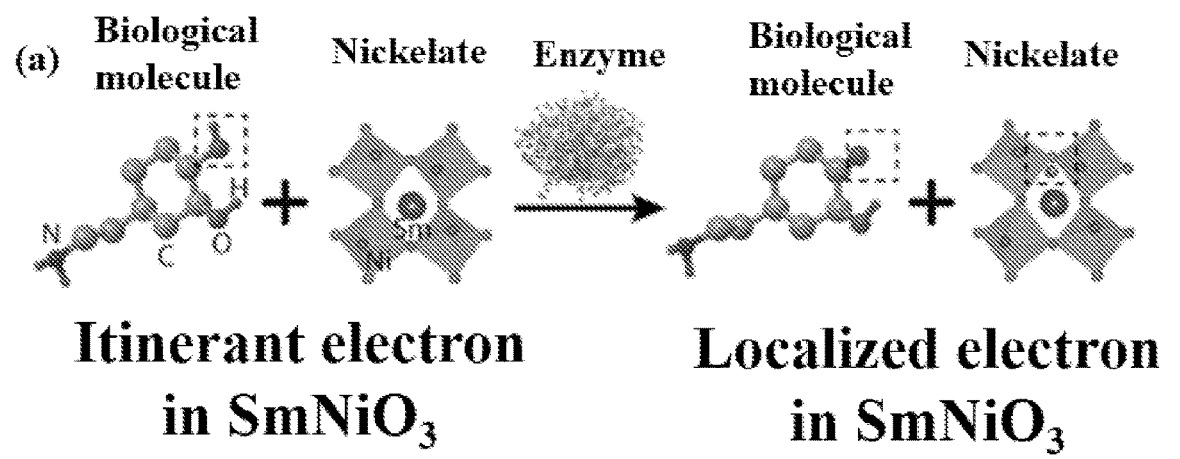
FIG. 2. (a) Sensing mechanism of the perovskite nickelate device. After the hydrogens are transferred to the perovskite nickelate from biological molecules, they donate electrons to the Ni and increase device resistance through electron localization. (b) Schematic figure of the sensing device in biological fluid. Hydrogen from biological molecules can be transferred to the perovskite nickelate sensor with the help of enzymes anchored on the electrode (Au) surface.
Figure 2:
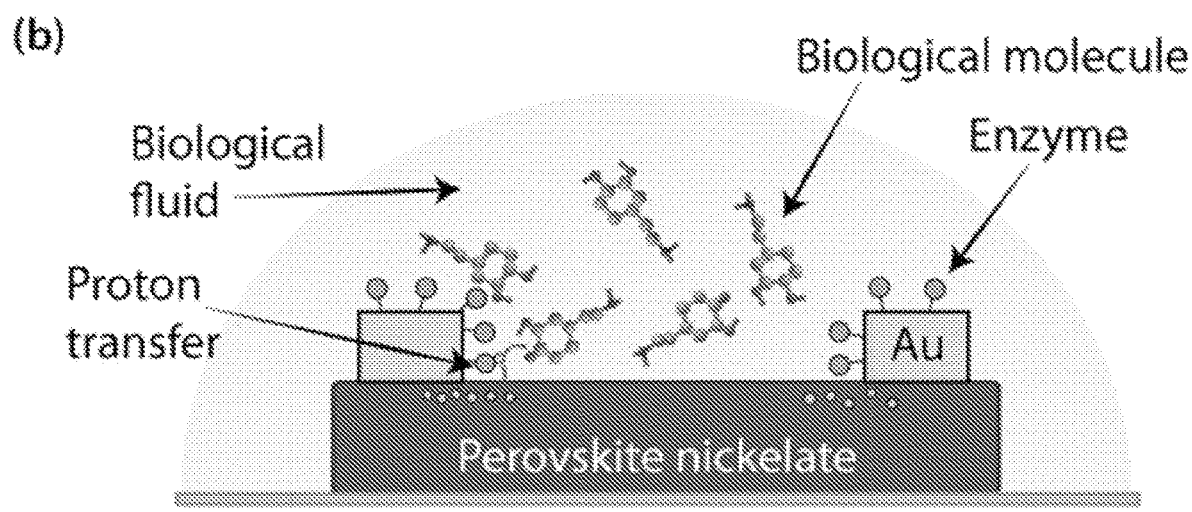

This disclosure provides a new device and system to detect biological molecules (such as glucose and dopamine) down to ultra-low concentrations. This device is based on rare earth perovskite nickelate $RNiO_3$ (R can be Sm, Nd, Eu, Gd, Dy, Y, Lu, Pr, La, etc). FIG. 2 shows the sensing mechanism and device where the electrical resistance of the device changes (increases) with the presence of biological molecules. In this sensing process, hydrogen atoms from the biological molecules are first transferred to an enzyme, and then into the $RNiO_3$ lattice. This process occurs spontaneously without the need for any external energy input. The hydrogen then bonds with oxygen anions and occupies interstitial sites among the oxygen octahedra in $RNiO_3$, contributing an electron to the d orbitals of nickel. As a result, the singly occupied Ni $e_g$ orbitals in glucose-reacted $RNiO_3$ become doubly occupied and the additional electron in the $e_g$ orbital imposes large on-site Mott-Hubbard electron-electron repulsion, leading to localization of the charge carriers and resistivity increase. Such a hydrogen-induced conduction suppression serves as a unique and ultra-sensitive platform for chemical transduction at the interface between the nickelate films and biological molecules. Schematic figure of the enzyme-$RNiO_3$ device is presented in FIG. 2 (b). The enzymes are anchored on a gold electrode via cystamine bonding and transfer hydrogen from biological molecules to the perovskite channel. The sensing function can be initiated by adding biological molecules on top of the device surface.

Figure 3:
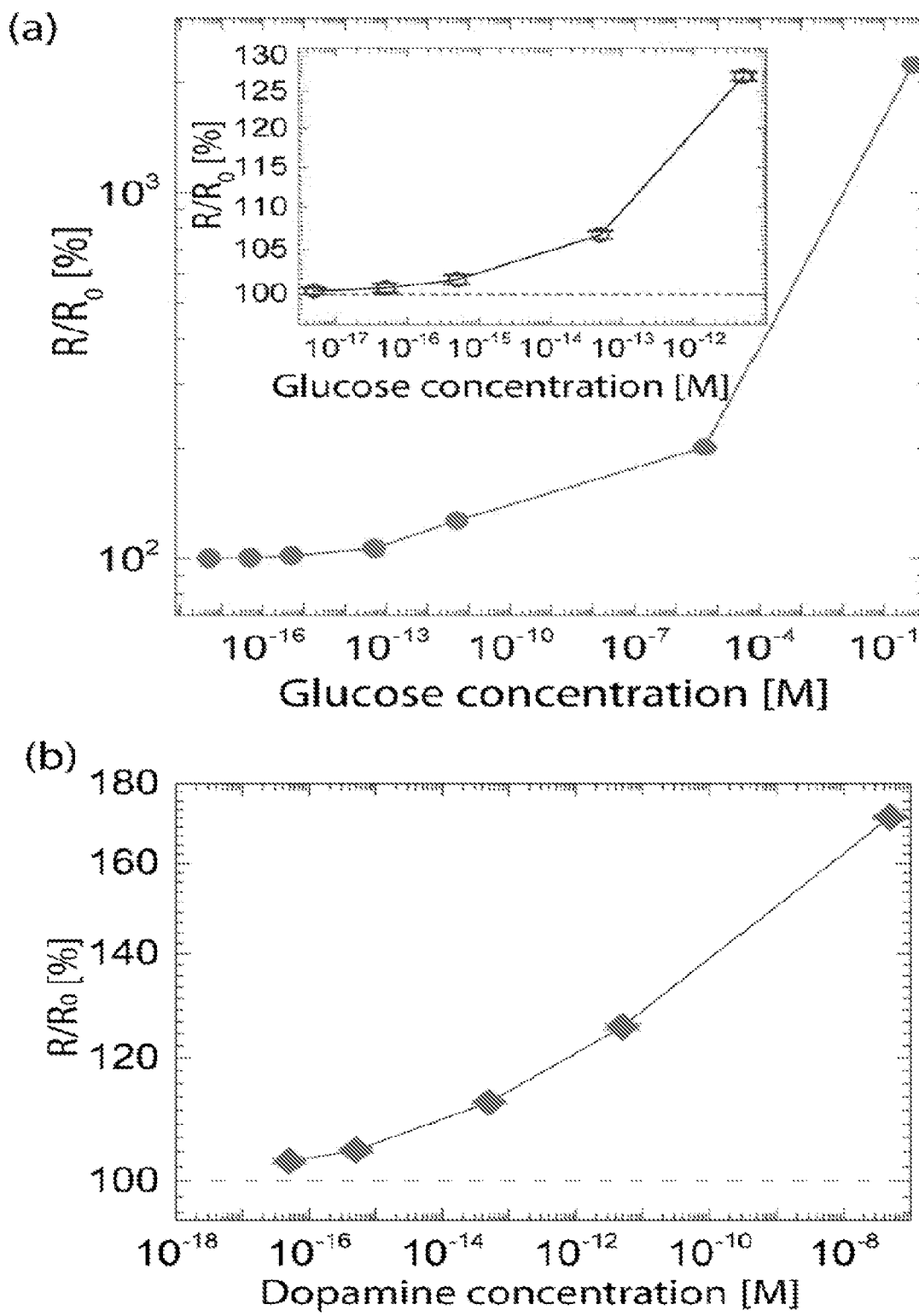
FIG. 3. (a) The response of the perovskite nickelate device to glucose solution in deionized water with different concentrations. The response is represented as a resistance ratio ($R/R_0$) before and after the reaction. (b) The response of the perovskite nickelate device to dopamine solution in deionized water with different concentrations. The response is represented as a resistance ratio ($R/R_0$) before and after the reaction.

After the biological molecules were added, the resistance of the perovskite nickelate device increased, due to the hydrogen transfer and its consequential electron localization as described in FIG. 2. The perovskite nickelate devices are highly responsive to dilute biological molecule concentrations and showed good selectivity. For the responsivity test, the perovskite nickelate devices were soaked in glucose and dopamine solutions with different concentrations for one hour and then the resistance ratio ($R/R_0$) was plotted in FIG. 3. In all the cases, the device resistance increased after the reaction, and $R/R_0$ becomes larger with increasing glucose concentration, and the detection limit is determined as $5 \times 10^{-16}$ M and $5 \times 10^{-17}$ M for glucose and dopamine, respectively (signal to noise ratio >3). The high detection limit in our perovskite nickelate devices is a unique attribute of strong electron correlations, a quantum mechanical effect wherein miniscule perturbation to the electron occupancy of orbitals can result in giant modulation of the transport gap. The devices were also found functional at body temperature (37° C.) and artificial cerebrospinal fluid (ACSF) environment.

The advantages of this technique include sensing biomolecules (such as dopamine and glucose) down to ultralow concentration, one order better than current state of the art techniques. Additionally, the sensing process is spontaneous, and no external energy is required in this process.

It is contemplated that strongly correlated oxides (such as but not limited to rare earth perovskite nickelate, and related transition metal oxides such as NiO, FeOx) are used as biomolecule sensors.

Without limiting to any particular theory, it is contemplated to use the strong election correlation effect in this class of materials to achieve high detection limit.

Exemplified but not limited to any particular theory, enzymes or other catalysts that facilitate proton transfer between bio-molecules and strongly correlated oxides is shown to be effective to sense bio-molecules.

Without being limited by any theory, it is also contemplated that other than resistivity change of strongly correlated oxides due to the proton transfer, change of optical, magnetic and thermal properties can also be utilized as possible sensing means.

Arrays of such devices can be fabricated to design large scale circuits on a chip to rapidly sense bio-molecules. Micro-fluidic channels can be integrated with such devices to direct flow of fluids onto the surfaces and sense presence of bio-matter. Various enzymes can be positioned at discrete devices and simultaneously several classes of bio-molecules can be sensed in a single chip. This can help rapidly identify bio-matter for health sciences such as diabetes or sweat or urine, blood monitoring. The devices can also be integrated into wearable electronic platforms for personal health monitoring.

EXAMPLES

Example 1. Fabrication of the Perovskite Nickelate Bio-Sensor Device

Perovskite nickelate films were grown using sputtering. Before deposition, $LaAlO_3$ substrates were rinsed by acetone and isopropanol, after which the substrates were dried by nitrogen. Co-sputtering of rare earth and Ni targets were performed with R at a radio frequency (RF) power at 170 W, and Ni at direct current (DC) power at 70 W. This growth condition ensures a stoichiometric ratio of R to Ni cations as characterized by energy-dispersive X-ray spectroscopy (EDS). The growth was carried out at room temperature with a background pressure of argon and oxygen mixture at 5 mTorr. Then the film was annealed at 500° C. for 24 hours under 100 bar of $O_2$ in a home-built high-pressure tube furnace. Au electrodes (50 nm thick with 3 nm Ti adhesion layer) were deposited using electron beam evaporation, and the devices were fabricated with shadow masks (500 μm gap). The GOx enzyme is selective to glucose oxidation while the horseradish enzyme (HRP) can be used to study dopamine release. To anchor the GOx enzyme and HRP enzyme respectively to the Au electrode surface, the SNO devices were first immersed in 10 mM cystamine solution for 2 hours at room temperature in dark. The GOx enzyme (Sigma-Aldrich catalog number G6125), HRP enzyme (Sigma-Aldrich catalog number P8375) and cystamine were purchased from Sigma-Aldrich Corporation. The SNO devices were then rinsed with DI water to remove the unreacted cystamine and dried with compressed air. Next, the glucose oxidase (GOx) was oxidized in order to conjugate to the cystamine on the Au surface. For this purpose, 30 mg sodium metaperiodate was added into 20 μM GOx solution (in 5 mL 0.1 M pH 6.8 Sodium Phosphate buffer). The mixture was incubated in 4° C. for 1 hour. Then 6.97 μL ethylene glycol was added into the mixture and incubated at room temperature for 30 mins to stop the reaction. This product was purified by PD-10 desalting column (GE Healthcare) to collect oxidized GOx as well as changing the buffer back to 0.1 M pH 6.8 Sodium Phosphate. The reacted SNO device was immersed in the collected GOx solution for 1 hour at 4° C. and then rinsed with DI $H_2O$. The device was then dried by compressed air and stored at 4° C. ready for use.

Example 2. Glucose Detection

Figure 1:
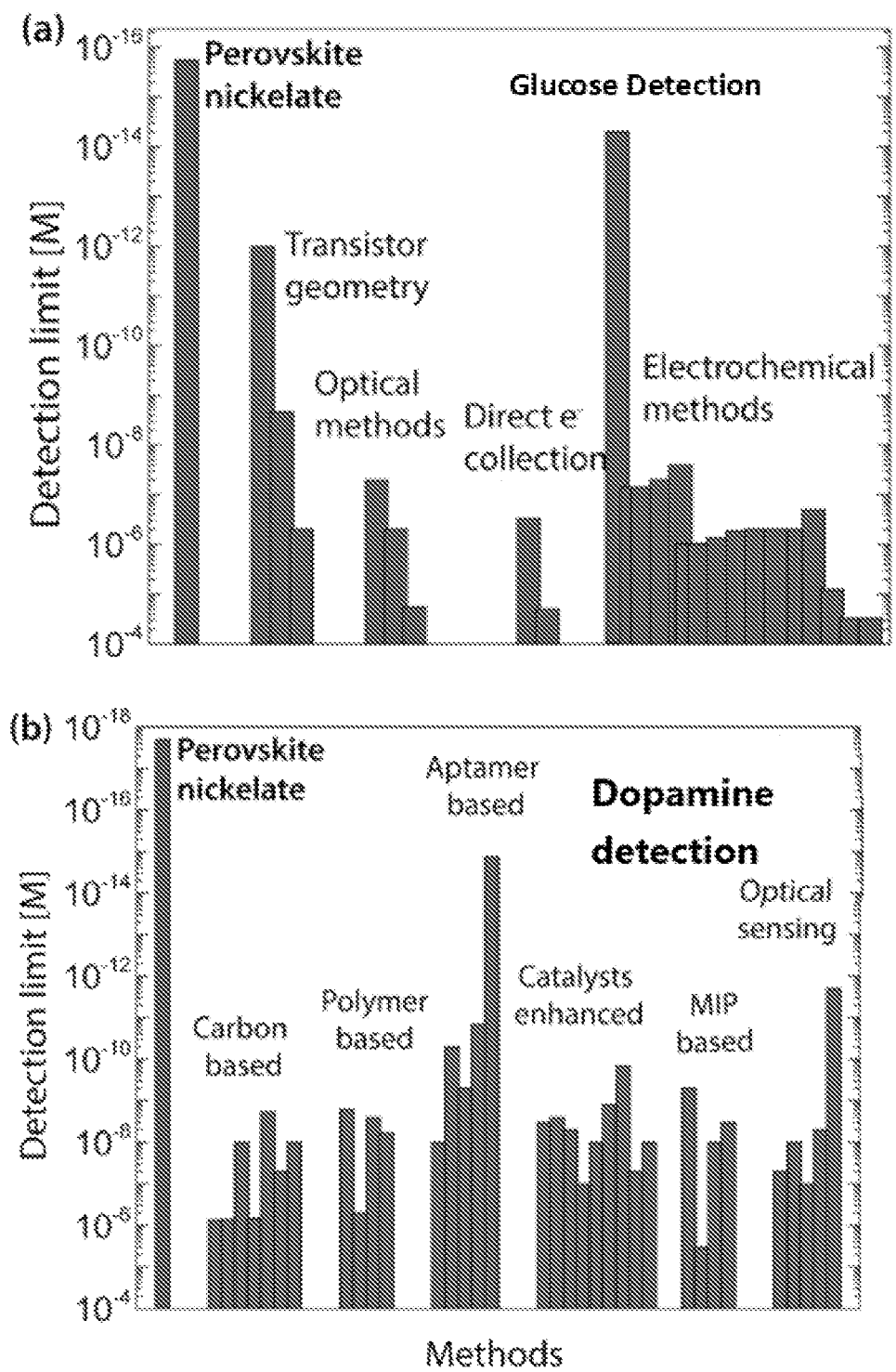
FIG. 1. State of the art summary of sensing mechanisms and their detection limit for (a) glucose and (b) dopamine molecules.

As shown in FIG. 1 (a), literature reports on glucose sensing mechanisms can be summarized into four categories: field effect transistor devices, optical methods, direct electron ($e^-$) collection, and electrochemical methods. The field effect transistor devices utilize gate voltage signal from the glucose reaction to modulate the channel conductance for glucose detection. Optical methods were performed by monitoring the optical emission/properties change at certain wavelength that is specific to the glucose reaction. Direct electron collection measures the glucose concentration by directly collecting the electron signal in certain glucose reactions. Electrochemical methods involve cyclic voltammetry to detect the reduction/oxidation peaks of glucose. The glucose detection limit is typically between $10^{-6}$ to $10^{-8}$ M, with the highest value being $10^{-12}$ M for the transistor device, and $2 \times 10^{-15}$ M for the voltage based electrochemical method with a specially designed reaction cell. The mechanism reported in this work is based on extreme electron localization in $SmNiO_3$ by carrier doping and has a detection limit of $\sim 5 \times 10^{-16}$ M.

Example 3. Dopamine Detection

As shown in FIG. 1(b), literature reports on dopamine sensing mechanisms can be summarized into six categories: carbon-based methods, polymer-based methods, aptamer-based methods, catalyst-enhanced methods, molecular imprinted polymer (MIP) based methods and optical sensing. Carbon-based materials such as carbon nanotubes and graphene can be used to detect dopamine through electrical and electrochemical measurements. Polymer based sensors are used due to their biological compatibility. In the Aptamer based methods, short DNA or RNA oligomers are specially designed so that they bind with dopamine for its detection. Catalysts enhanced methods use catalysts to modify electrodes (such as polymer, graphene and carbon fiber etc.), and enhance sensor performance. In the molecular imprinted polymer (MIP) methods, functional monomers first polymerize with template molecules, and then the template molecules are removed. In this way, the detection surface area is increased, and the target molecules bind to the functional sites more preferentially. The optical sensing methods detect local change in optical properties or fluorescence due to the presence of dopamine. The mechanism reported in this work utilizes strong electron correlations induced by hydrogen doping leading to electron localization in $SmNiO_3$ and has a detection limit of $\sim 5\times10^{-17}$ M.

The invention claimed is:

1. A method of detecting a biomarker in a biological fluid, comprising:
   (i) providing a device comprising the following components:
      a perovskite nickelate film comprising $RNiO_3$, wherein said perovskite nickelate film is configured as a lattice or with micro-fluidic channels, wherein R is selected from the group consisting of Sm, Nd, Eu, Gd, Dy, Y, Lu, Pr, and La; and
      an enzyme horseradish peroxidase (HRP) for detection of the biomarker dopamine conjugated to a conductive material, wherein said conductive material is deposited on said perovskite nickelate film, wherein said enzyme facilitates hydrogen transfer from said biomarker to said perovskite nickelate film and reduces conductivity at the interface between the perovskite nickelate film and said biomarker;
   (ii) measuring the resistance reading $R_0$ between the device and the conductive material;
   (iii) immersing the device in the biological fluid, wherein the biological fluid is cerebrospinal fluid;
   (iv) measuring the resistance reading R between the device and the conductive material after the immersing step; and
   (v) determining a resistance ratio $R/R_0$ using the resistance readings of step (iv) and step (ii), respectively, whereupon the biomarker dopamine present in the cerebrospinal fluid is identified when the resistance ratio $R/R_0$ is greater than 1.

2. The method according to claim 1, which is conducted at room temperature or at body temperature.

3. The method according to claim 1, wherein the detection limit for detecting dopamine is about $10^{-17}$ M.

4. The method according to claim 1, wherein the device comprises Au as the conductive material.

5. The method according to claim 4, wherein said horseradish peroxidase is conjugated to the conductive material via a reaction with cystamine.

6. The method according to claim 1, wherein the device is configured as arrays with circuits on a single chip to simultaneously sense biomarkers that corresponding enzymes specifically recognize and facilitate hydrogen transfer.

7. The method according to claim 1, which is conducted spontaneously with the biological fluid immersion of the device and free of external energy input.

* * * * *